United States Patent [19]

Vyas et al.

[11] Patent Number: 5,099,016
[45] Date of Patent: Mar. 24, 1992

[54] SUBSTITUTED 7-OXOMITOSANES

[75] Inventors: Dolatrai M. Vyas; Terrence W. Doyle, both of Fayetteville; Richard A. Partyka, Liverpool, all of N.Y.

[73] Assignee: Bristol-Myers Company, New York, N.Y.

[21] Appl. No.: 485,399

[22] Filed: Feb. 26, 1990

Related U.S. Application Data

[60] Division of Ser. No. 267,601, Nov. 7, 1988, Pat. No. 4,927,943, which is a division of Ser. No. 160,474, Feb. 25, 1988, Pat. No. 4,814,445, which is a continuation of Ser. No. 744,570, Jun. 17, 1985, abandoned, which is a continuation-in-part of Ser. No. 646,888, Sep. 4, 1984, abandoned.

[51] Int. Cl.$^5$ .................. C07D 487/14; A61K 31/40
[52] U.S. Cl. ...................................... 544/132; 548/422
[58] Field of Search ...................... 548/422; 544/132; 514/310

[56] References Cited

U.S. PATENT DOCUMENTS 4,888,341 12/1989 Remers et al. ...................... 548/422

Primary Examiner—Nicholas S. Rizzo
Attorney, Agent, or Firm—Aldo A. Algieri

[57] ABSTRACT

The present invention provides novel mitomycin analogs containing a disulfide group and processes for the preparation thereof. These compounds are mitomycin A analogs in which the 7-alkoxy group bears an organic substituent incorporating a disulfide group. Mitomycin A is an antibiotic of established utility, and the 7-O-substituted mitosane analogs thereof have similar utility.

1 Claim, No Drawings

SUBSTITUTED 7-OXOMITOSANES

This application is a divisional of a co-pending application Ser. No. 267,601, filed Nov. 7, 1988, now U.S. Pat. No. 4,927,947 which is a divisional of Ser. No. 160,474, filed Feb. 25, 1988, now U.S. Pat. No. 4,814,445, which is a continuation of Ser. No. 744,570, filed June 17, 1985, abandoned which is a continuation-in-part of Ser. No. 646,888, filed Sept. 4, 1984, abandoned.

BACKGROUND OF THE INVENTION

1. Field of the Invention

The present invention provides novel mitomycin analogs containing a disulfide group (Class 260, Subclass 326.24) and processes for the preparation thereof. These compounds are mitomycin A analogs in which the 7-alkoxy group bears an organic substituent incorporating a disulfide group. The present invention also provides a method of producing mitomycin A and derivatives thereof (Class 260, Subclass 326.24). Mitomycin A is an antibiotic of established utility, and the 7-O-substituted mitosane analogs thereof have similar utility.

Nomenclature—The systematic Chemical Abstracts name for mitomycin A based on the recent revision [Shirhata et al., *J. Am. Chem. Soc.*, 105, 7199 (1983)] is:

[1aS-(1aβ, 8β, 8aα, 8βbβ)]-8-[((aminocarbonyl)oxy)-methyl]-6,8a-dimethoxy-1,1a,2,8,8a,8b-hexahydro-5-methyl]-arizino[2',3',3,4,]pyrrolo[1,2-a]indole-4,7-dione according to which the azirinopyrroloindole ring system is numbered as follows:

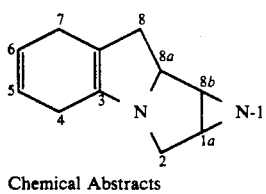

Chemical Abstracts

A trivial system of nomenclature which has found wide use in the mitomycin literature identifies the foregoing ring system including several of the characteristic substituents of the mitomycins as mitosane.

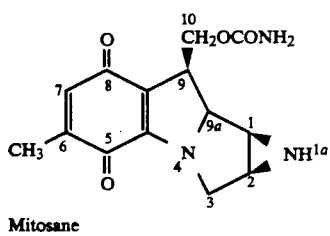

Mitosane

According to this system, mitomycin A is 7,9a-dimethoxymitosane and mitomycin C is 7-amino-9a-methoxymitosane. As to the stereochemical configuration of the products of this invention, it is intended when identifying them by the root name "mitosane" or by structural formula to identify the stereochemical configuration thereof as the same as that of mitomycin A or C.

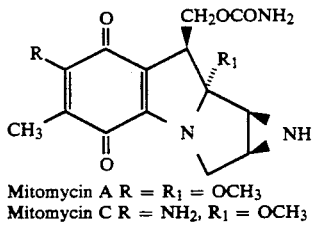

Mitomycin A R = R₁ = OCH₃
Mitomycin C R = NH₂, R₁ = OCH₃

2. Disclosure Statement

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin ® Bristol Laboratories, Syracuse, New York 13221, Physicians' Desk Reference 37th Edition, 1983, pp. 747 and 748). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al. of Lederle Laboratories Division American Cyanamid Company, *J. Am. Chem. Soc.*, 84, 3185-3187 (1962). One of the chemical transformations used in this structure study to relate mitomycin A and mitomycin C was the conversion of the former, 7,9a-dimethoxymitosane, by reaction with ammonia to the latter, 7-amino-9a-methoxymitosane. Displacement of the 7-methoxy group of mitomycin A has proven to be a reaction of considerable interest in the preparation of antitumor active derivatives of mitomycin C. Recently the stereochemical configurations of positions 1, 1a, 8a and 8b have been shown to be as indicated above with respect to the Chemical Abstracts nomenclature [Shirhata et al., *J. Am. Chem. Soc.*, 105, 7199-7200 (1983)]. The earlier literature- refers to the enantiomer.

The following articles and patents deal inter alia with the conversion of mitomycin A to a 7-substituted amino mitomycin C derivative having antitumor activity. The object of this research was to prepare derivatives which were more active, and particularly which were less toxic than mitomycin C:

Matsui et al., *J. Antibiotics*, XII, 189-198 (1968);
Konishita et al., *J. Med. Chem.* 15, 103-109 (1971);
Iyengar al., *J. Med. Chem.*, 24, 975-981 (1981);
Iyengar, Sami, Remers and Bradner, Abstracts of Papers, 183rd Annual Meeting of the American Chemical Society, Las Vegas, Nevada, March 1982, Abstract No. MEDI 72;
Cosulich et al., U.S. Pat. No. 3,332,944, issued July 25, 1967;
Matsui et al., U.S. Pat. No. 3,420,846, issued Jan. 7, 1969;
Matsui al., U.S. Pat. No. 3,450,705, issued June 17, 1969;
Matsui et al., U.S. Pat. No. 3,514,452, issued May 26, 1970;
Nakano al., U.S. Pat. No. 4,231,936, issued Nov. 4, 1980;
Remers, U.S. Pat. No. 4,268,676, issued May 19, 1981.

The following patent applications deal with the preparation of 7-substituted amino mitomycin C derivatives in which the substituent incorporates a disulfide linkage.

Kono et al., European Patent Application No. 116,208 (1984);

Vyas et al., U.K. Patent Application No. 2,140,799 (1984).

7-Alkoxy substituted mitosanes related structurally to mitomycin A are described as useful antibiotics having activity in experimental animal tumors in an article by Urakawa et al., *J. Antibiotics*, 23, 804–809 (1980).

Mitomycin C is the principal mitomycin produced by fermentation and is the commercially available form. Current technology for the conversion of mitomycin C to mitomycin A suffers from a number of deficiencies. Hydrolysis of mitomycin C to the corresponding 7-hydroxy-9a-methoxy-mitosane, and then methylation of that substance requires diazomethane, a very hazardous substance to handle on a manufacturing scale, and the 7-hydroxy intermediate is very unstable [Matsui et al., *J. Antibiotics*, XXI, 189–198 (1968)]. One attempt to avoid these difficulties involves the use of 7-acyloxymitosanes (Kyowa Hakko Kogyo KK Japanese Patent No. J5 6073-085, Farmdoc No. 56227 D/31). Alcoholysis of mitomycin A as described by Urakawa et al., *J. Antibiotics*, 23, 804–809 (1980) is limited to the production of only specific 7-alkoxy structural types by the availability and reactivity of the alcohol starting materials.

SUMMARY OF THE INVENTION

The present invention is concerned with a group of mitomycin A analogs having a dithio organic substituent incorporated in the alkoxy group at the 7-position. These compounds may be represented by the following general formula

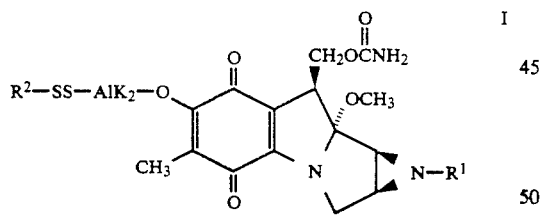

wherein $R^2$ is an organic group, viz. The structural component of an organic thiol of the formula $R^2SH$, and $Alk_2$ and $R^1$ have the meanings given below. These compounds are alternatively described by Formulas II and III.

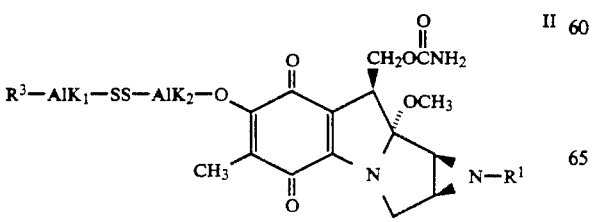

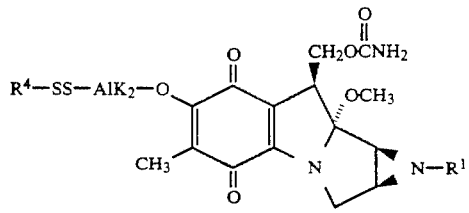

wherein:

$Alk_1$ is a straight or branched chain alkylene group having 1 to 6 carbon atoms when $R^3$ is joined thereto through a carbon atom thereof, and 2 to 6 carbon atoms when $R^3$ is joined thereto through a sulfur, oxygen or nitrogen atom thereof, and $R^3$ and 13 SS— are in that instance joined to different carbon atoms, $Alk_2$ is a straight or branched chain alkylene group having 2 to 6 carbon atoms optionally bearing an A substituent wherein the sulfur and oxygen atoms connected thereto and any optional A substituent connected thereto through oxygen, sulfur or nitrogen are attached to different carbon atoms of $Alk_2$, wherein said A substituent is selected from the group consisting of one or two $C_{1-6}$ alkyl, $C_{1-6}$ alkanoyl, $C_{1-6}$ alkoxy, halogen, $C_{1-6}$ alkoxycarbonyl, cyano, $C_{1-6}$ alkylamin $C_{1-6}$ -dialkylamino, $C_{1-6}$ alkanoylamino and $C_{1-6}$ alkoxycarbonyl, $Alk_1$ and $Alk_2$ may contain a double bond, $R^1$ is hydrogen, lower alkyl, lower alkanoyl, benzoyl or substituted benzoyl wherein said substituent is lower alkyl, lower alkoxy, halogen, amino or nitro, $R^3$ is selected from the group consisting of halogen, carboxy, alkanoyloxy having 1 to 7 carbon atoms, hydroxy wherein the oxygen atom is connected to $Alk_1$ having 3 to 6 carbon atoms, alkylamino or dialkylamino having 1 to 12 carbon atoms, N-alkoxy-alkylamino having 2-7 carbon atoms, alkanoylamino having 1-7 carbon atoms, benzoylamino or B-substituted benzoylamino, naphthoylamino or B-substituted naphthoylamino, phenylamino or B-substituted phenylamino, cycloalkyl or B-substituted cycloalkyl each having 3 to 8 ring members, cycloalkenyl or B-substituted cycloalkenyl each having 5 to 8 ring members, phenyl or B-substituted phenyl, naphthyl or B-substituted naphthyl, a heterocyclic group selected from the group consisting of heteroaromatic and heteroalicyclic groups having from 1 to 2 rings, from 3 to 8 ring members in each ring and from 1 to 2 heteroatoms in each ring selected from oxygen, nitrogen and sulfur, pyridylamino or thiazolylamino, alkoxy or alkylthio each having 1 to 6 carbon atoms, alkoxycarbonyl or alkylaminocarbonyl each having 2 to 7 carbon atoms, aminocarbonyl, phenoxycarbonyl or B-substituted phenoxycarbonyl, phenoxy or B-substituted phenoxy! naphthoxy or B-substituted naphthoxy, alkoxycarbonylamino having 2 to 6 carbon atoms, ureido (—NHCONH₂), N-alkylureylene (—NHCONHalkyl) having 2 to 7 carbon atoms, $N^3$-haloalkylureylene having 3 to 7 carbon atoms, $N^3$-haloalkyl-$N^3$-nitrosoureylene having 3 to 7 carbon atoms, dialkylaminocarbonyl having 3 to 13 carbon atoms, dialkylaminoalkoxy having 4 to 13 carbon atoms, alkanoylaminoalkoxy having 3 to 7 carbon atoms and hydroxyalkylamino or N,N-dihydroxyalkyl amino each having 2 to 8 carbon atoms, wherein said B substituent is selected from the group consisting of one or two lower alkyl, lower alkanoyl, lower alkoxy, halogen, amino, carboxy, hydroxy and nitro groups, and $R^4$ is selected from the group consisting of alkyl having 1 to 12 carbon atoms, alkenyl or alkynyl each having 3 to 12 carbon atoms, cycloalkyl or B-substituted cycloalkyl having 3 to 8 ring members, cycloalkenyl or B-substituted cycloalkenyl each having 5 to 8 ring members, phenyl or B-substituted phenyl, naphthyl or B-substituted naphthyl, a heterocyclic group selected from the group consisting of heteroaromatic and heteroalicyclic groups having from 1 to 2 rings, from 3 to 8 ring members in each ring, and from 1 to 2 eteroatoms in each ring selected from oxygen, nitrogen and sulfur, provided that the heterocyclic group is connected through a carbon atom which is attached to at least another carbon atom (i.e., the carbon atom attached to the —SS— may not itself be attached to two other heteroatoms), wherein said B substituent is selected from the group consisting of one or two lower alklyl, lower alkanoyl, lower alkoxy, halogen, amino, carboxyl, hydroxy or nitro groups, and $R^4$ and the adjacent sulfur atom together constitute S-cysteinyl wherein said S-cysteinyl group may be esterified, salified or joined within a non-toxic and non-allergenic peptide, or a nontoxic pharmaceutically acceptable salt thereof.

The compounds of the present invention are inhibitors of experimental tumors in animals. In particular, the substances identified herein as compounds of Example Nos. 17, 20 and 21–34 are novel substances. They are employed in a manner similar to mitomycin C. The dosages employed are adjusted in proportion to their toxicities relative to the toxicity of mitomycin C. In cases where the new compound is less toxic, a higher dose is employed.

In a further aspect of the present invention, there is provided a new process for the production of mitosanes of Formulas II and III. This new process comprises reacting a mitosane of Formula IV

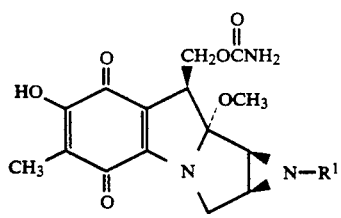

with a triazene of Formula V or Formula VI

Ar—N=N—NH—Alk₂—SS—AlK₁—R³  V

Ar—N=N—NH—Alk₂—SS—R⁴  VI wherein $R^1$, $R^3$, $R^4$, $Alk_1$ and $Alk_2$ are as defined above and Ar is the organic residue of a diazotizable aromatic amine.

in a variation of the present invention, there is provided an alternate process for the production of mitosanes of Formulas II and III. This process comprises reacting a thiol of Formula VII or VIII $R^3Alk_1SH$   $R^4SH$
VII   VIII with a mitosane derivative of Formula Ib

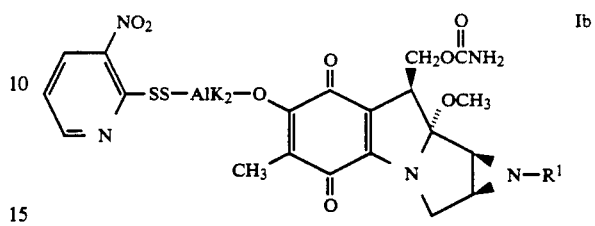

The disulfide mitosanes of Formula Ib are prepared by the triazene method described herein. More specifically, the mitosane of Formula Ib wherein $Alk_2$ is ethylene and $R^1$ is hydrogen is described in Example 20 and in co-pending application Ser. No. 646,888, filed Sept. 4, 1984.

In another aspect of the present invention, there is provided an improved method for preparing compounds having Formula IX

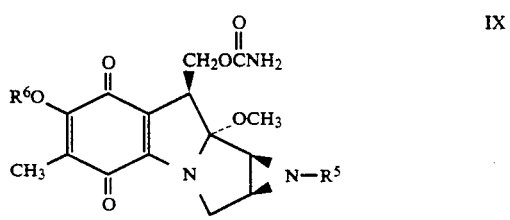

wherein:
$R^5$ is hydrogen, or $C_{1-6}$ alkyl, and
$R^6$ is $C_{1-12}$ alkyl or substituted $C_1$ alkyl, $C_{3-12}$ cycloalkyl or substituted $C_{3-12}$ cycloalkyl wherein the carbon atom thereof which is attached to the mitosane 7-oxygen atom bears from 1 to 2 hydrogen atoms and said substituents are selected from the group consisting of halogen, $C_{1-6}$ alkoxy, $C_{1-6}$ alkanoyl, $C_{6-14}$ aroyl, cyano, trihalomethyl, amino, $C_{1-6}$ monoalkylamino, $C_{2-12}$ dialkylamino, $C_{6-12}$ aryl, $C_{6-12}$ aryloxy, $C_{1-6}$ alkanoyloxy, $C_{7-14}$ aroyloxy, heterocyclo having 1 or 2 rings and from 5 to 12 ring atoms including up to 4 heteroatoms selected from nitrogen, oxygen, and sulfur, and wherein each of said alkoxy, alkanoyl, aroyl, aryl, aryloxy, alkanoyloxy, aroyloxy, and heterocyclo substituents optionally contains from 1 to 2 substituents selected from halogen, $C_{1-6}$ alkoxy, $C_{1-6}$ alkanoyl, cyano, trihalomethyl, amino, $C_{1-6}$ alkylamino, or $C_{2-12}$ dialkylamino groups.

Many of the compounds of Formula IX are known compounds having inhibitory activity against experimental animal tumors in vivo. A number of novel compounds conforming to Formula IX have also been prepared by this process, and are considered part of the present invention. In particular the substances identified herein as compounds of Example Nos. 14, 15, 16 and 19 are novel substances, and also have antitumor activity against experimental animal tuxors. These compounds are part of the present invention. They are employed in a manner similar to mitomycin C. The dosages employed are adjusted in proportion to their toxicities relative to the toxicity of mitomycin C. In cases where the new compound is less toxic, a higher dose is employed.

The new process for production of compounds of Formula IX comprises reacting a mitosane of Formula X

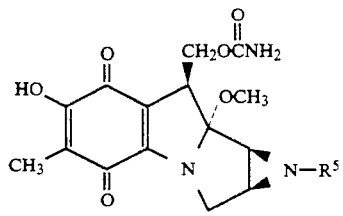

with a triazene of Formula XI $$Ar-N=N-NH-R^6 \quad XI$$

wherein $R^5$ and $R^6$ are as defined above and Ar is not organic residue of a diazotizable aromatic amine.

The terms "lower alkyl", "lower alkoxy" and "lower alkanoyl" as used herein and in the claims (unless the context indicates otherwise) mean straight or branched chain alkyl, alkoxy or alkanoyl groups containing from 1 to 6 carbon atoms such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine. The term "nontoxic pharmaceutically acceptable salt" is intended to include salts of the compounds of Formulas I and II with any nontoxic pharmaceutically acceptable acid or base. Such acids are well-known and include hydrochloric, hydrobromic, sulfuric, sulfamic, phosphoric, nitric, maleic, fumaric, succinic, oxalic, benzoic, methanesulfonic, tartaric, citric, camphorsulfonic, levulinic and the like. Such basses are well-known and include, e.g. nontoxic metallic salts such as sodium, potassium, calcium and magnesium, the ammonium salt and salts with nontoxic amines, e.g. trialkylamines, procaine, dibenzylamine pyridine, N-methylmorpholine, N-methylpiperidine and the like. The salts are made by methods known in the art.

DESCRIPTION OF THE INVENTION

The present invention provides a new process for the preparation of compounds of Formula IX which comprises reacting a mitosane of Formula X with a triazene of Formula XI as shown in Scheme 1.

Scheme 1

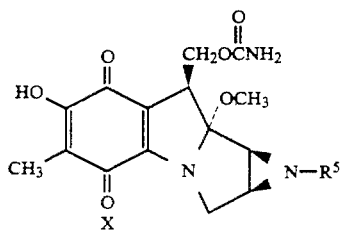

-continued $$+ Ar-N=NH-R^6 \longrightarrow IX$$
$$XI$$

wherein $R^5$ and $R^6$ are as defined above and Ar is the organic residue of a diazotizable aromatic amine.

The 1-substituted-3-aryltriazenes of Formula XI and more specifically 1-alkyl-3-aryltriazenes make up a class of reagent which are known to be useful for reacting with carboxylic acids to form the corresponding lower alkyl esters. 1-Methyl-3(4-methylphenyl)triazene may be prepared according to the general procedures described by E. H. White et al. in *Org. Syn.*, 48, 102–105 (1968) and as described herein in Procedure 1. However this procedure works well only with water-soluble amines, and a second procedure which is described by E. H. White et al., *Tetrahedron Letters*, No. 21, 761 (1961) and also described herein in Procedure 2 is more suitable for the preparation of triazenes of water-insoluble amines.

The reagent 1-methyl-3-(4-methylphenyl)triazene prepared in the above fashion has been previously employed to prepare methyl esters of carboxylic acids such as 2,4-dinitrobenzoic acid [E. H. White et al. *Org. Syn.*, 48, 102–105 (1968)] and cephalosporanic acids which yields the desired $\Delta^3$-compound without isomerization to the $\Delta^2$-isomer [Mangia, *Tetrahedron Letters*, No. 52, pp. 5219–20 (1978)]. The reagent has also been employed to produce a 3-methoxy-cephalosporin derivative by reaction with the corresponding 3-hydroxy-3-cephem-4-carboxylate in benzene solution at the reflux temperature. (Wiederkeher et al. U.S. Pat. No. 4,069,324 issued Jan. 17, 1978).

Other 1-(lower alkyl)-3-aryltriazenes of Formula XI may be prepared similarly by reaction of other lower alkyl amines with aryldiazonium salts in similar fashion. Any arylamine having 6 to 12 carbon atoms which readily forms a diazonium salt may be used as the source of the aryl portion of the 1,3-disubstituted triazene. Some examples of triazenes produced in this fashion and used in the present invention are:

1-(n-butyl)-3-(4-methylphenyl)triazene;
1-(1-methylethyl)-3-(4-methylphenyl)triazene;
1-(4-methylphenyl)-3-[2-(4-morpholinyl)ethyl]triazene;
1-(4-methylphenyl)-3-[2-(2-pyridyl)ethyl]triazene;
1-(2-benzylthioethyl)-3-(4-methylphenyl)triazene;
1-(4-chlorophenyl)-3-(2-methoxyethyl)triazene;
1-(4-chlorophenyl)-3-(1,3-dioxol-2-ylmethyl)triazene;
1-(4-chlorophenyl)-3-(tetrahydrofuran-2-ylmethyl)-triazene.

Other triazenes have been described in the literature which are suitable reactants for use in the present process to provide 7-(substituted alkoxymitosane) of Formula IX. Those described by T. A. Daniels et al., *Can. J. Chem.*, 55, 3751–3754 (1977) are exemplary.

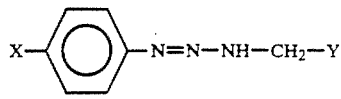

a X=H, Y=CN
b X=NO$_2$, Y=CN
c X=CO$_2$Me, Y=CN
d X=Ac, Y=CN
e X=NO$_2$, Y=CO$_2$Et f X=CO$_2$Me, Y=CO$_2$Et
g X=CO$_2$Me, Y=COPh
h X=NO$_2$, Y=—CH(OCH$_3$)$_2$

The following further exemplify suitable triazene starting materials of Formula XI for use in the present invention.

1(n-butyl)-3-(α-naphtyl)triazene
1(n-hexyl)-3-phenyltraizene
1-ethyl-3-(2,4-dimethylphenyl)traizene
1(1-methylethyl)-3-(4-methoxyphenyl)traizene For the preparation of mitomycin A, we prefer to use 3-methylethyl-1-(4-methoxyphenyl)traizene as methylating reagent. Preferably, at least two molecular proportions of the latter per molecular proportion of 7-hydroxy-9a-methoxymitosane are employed and the reaction is preferably carried out in a liquid organic solvent for the 7-hydroxy-9a-methoxymitosane starting material. Preferred solvents are the lower alkanols, lower alkanoic lower alkyl esters, the dilower alkyl ethers, the cyclic aliphatic ethers, and the lower polyhalogenated laiphatic hdyrocarbons. These solvents contain up to 6 carbon atoms, but those boiling at temperatures of less than 100° C. are preferred. Specific preferred solvents are methylene chloride, methanol, diethyl ether, ethyl acetate, and mixtures thereof. The reaction may be carried out at the reflux temperature of the reaction mixture or up to about 60° C. At temperatures in excess of this the mitosane reactant is inclined to decompose with a resultant reduction in yield. It is preferred to carry out the reaction at room temperature or below, for instance within the range of 0° C. to 25° C.

A convenient way to determine when the reaction is complete is by thin layer chromatography. Mitomycin A is deep purple in color and can be readily distinguished from the starting material and from by-products. In the solvent system methylene chloride/methanol (90/10) mitomycin A exhibits R$_f$=0.36. Chromatography on neutral alumina may be used for purification of the product.

The foregoing reaction conditions and precautions are generally applicable to the preparation of other 7-R$^6$O-mitosanes of Formula IX according to the present process.

The new process of the present invention utilizing 1-substituted-3-aryltriazenes may also be used to prepared compounds of the Formula II or III which comprises reacting a mitosane of Formula IV with a triazene of Formula V or VI as shown in Scheme 2.

Scheme 2

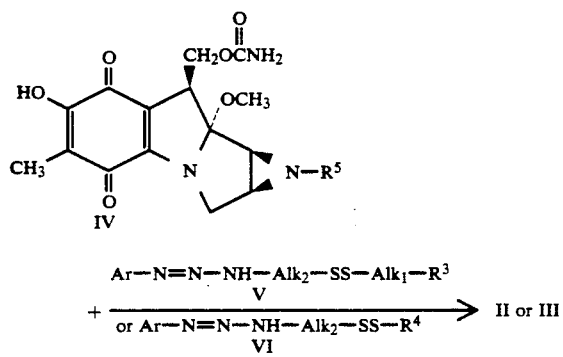

wherein R$^1$, R$^3$, R$^4$, Alk$_1$ and Alk$_2$ are as defined above, and Ar is the organic residue of a diazotizable aromatic amine.

Aryltriazenes of Formula V or VI may be prepared in a similar fashion as described above for the preparation of aryltriazenes of Formula XI expect that the alkyl amines utilized therein are replaced by aminodisulfides of Formula XII R$^2$—SS—Alk$_2$NH$_2$      XII which are alternatively described by Formulas XIII and XIV R$^3$—Alk$_1$—SS—Alk$_2$NH$_2$ and R$^4$—SS—Alk$_2$NH$_2$
XIII      XIV Aminodisulfides of Formula XIII and Formula XIV are known compounds and may be prepared by various methods. For instance, they may be made by reaction of the appropriate thiol R$^3$Alk$_1$SH or R$^4$SH with a Bunte salt of the formula NH$_2$Alk$_2$SSO$_3$Na      XV or with a sulfenylthiocarbonate of the formula

      XVI

Klayman et al., *J. Org. Chem.*, 29, 3737–3738 (1964) have prepared the following, by the Bunte salt method:

2-aminoethyl n-butyl disulfide;
2-aminoethyl n-hexyl disulfide;
2-aminoethyl n-octyl disulfide;
2-aminoethyl n-decyl disulfide;
2-aminoethyl phenyl disulfide.

Methanol was found to be the preferred reaction solvent for the reaction of the Bunte salt with the thiol. Reaction temperatures of 0° C. to −10° C. were found to be preferred using this solvent. Higher temperatures were necessary with other solvents. The chief drawback of this method is the formation of symmetrical disulfides as a by-product, presumably as a result of disporportionation of the desired mixed disulfide.

The mixed disulfide starting materials of Formulas XIII and XIV are preferably prepared via reaction of the appropriate method of S. J. Brois et al., *J. Am. Chem. Soc.*, 92, 7629–7631 (1970). Typically, this preparative procedure involves adding the thiol to a methanol solution of the amino-alkylsulfenylthiocarbonate of Formula XVI and allowing the reaction to proceed at a temperature in the range of from 0° C. to 25° C. Reaction times vary from virtually instantaneous to several hours depending upon the particular thiol employed. The progress of the reaction can be followed by measuring the presence of unreacted thiol in the reaction vessel. If the reaction is sluggish, a catalytic amount of triethylamine may be added as reaction accelerator.

The 1-(substituted disulfide)-3-aryltriazenes of Formula V or VI are prepared by the reaction of aminodisulfides of Formula XII with aryldiazonium salts in a similar fashion as described herein for the preparation of aryltriazenes of Formula XI. Any arylamine having 6 to 12 carbon atoms which readily forms a diazonium salt may be used as the source of the aryl portion of the 1,3-disubstituted triazene. Some examples of disulfide triazenes produced in this fashion and used in the present invention are 1-[2-(2-acetamidoethyldithiol)ethyl]-3-(4-mathyl-phenyl)triazene;

1-[2-(3-nitro-2-pyridyldithio)ethyl]-3-(4-methyl-phenyl)triazene.

The following further exemplify suitable triazene starting materials of Formula V or VI for use in the present invention.

1-[2-(3-nitro-2-pyridyldithio)ethyl]-3-(4-chloro-phenyl)triazene;

1-[2-(3-nitro-2-pyridyldithio)propyl]-3-(4-methyl-phenyl)triazene;

1-[2-(2-pyridyldithio)ethyl]-3-(4-methylphenyl)triazene;

1-[2-(phenyldithio)ethyl]-3-(4-methylphenyl)triazene;

1-[2-(butyldithio)ethyl]-3-(4-methylphenyl)triazene;

1-[2-(4-methoxyphenyldithio)ethyl]-3-(4-methyl-phenyl)triazene;

1-[2-(4-nitrophenyldithio)ethyl]-3-(4-methylphenyl)-triazene;

1-{2-[(2-benzoylaminoethyl)dithio]ethyl}-3-(4-methylphenyl)-triazene;

1-[2-(4-chloro-2-naphthyldithio)ethyl]-3-(4-methyl-phenyl)-triazene;

1-[2-(cyclopropylmethyldithio)ethyl]-3-(4-methyl-phenyl)triazene;

1-{2-[(2-phenoxyethyl)dithio]ethyl}-3-(4-methyl-phenyl)triazene.

In a preferred embodiment of the present invention, there is provided an alternate process for the preparation of disulfide mitosanes having the formula Ia

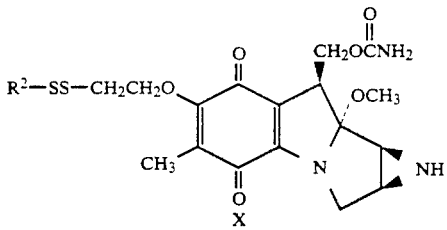

wherein $R^2$ is an organic group, viz. the structural component of an organic thiol of the formula $R^2SH$, which is alternatively described by $R^3Alk_1$ or $R^4$ wherein $R^3$, $R^4$ and $Alk_1$ are as defined above.

For the preparation of the disulfide mitosanes of Formula Ia, it is preferred to utilize the 9a-methoxy-7-[2-(3-nitro-2-pyridyldithio)ethoxy]mitosane of Formula XVII in a thiol exchange process with an appropriate organic thiol of the formula $R^2SH$ as shown in reaction Scheme 3. The driving force behind the formation of the disulfides of Formula Ia is the stability of the by-product, namely 3-nitro-2-mercaptopyridine, which solely exists as the thione XVIII.

Scheme 3

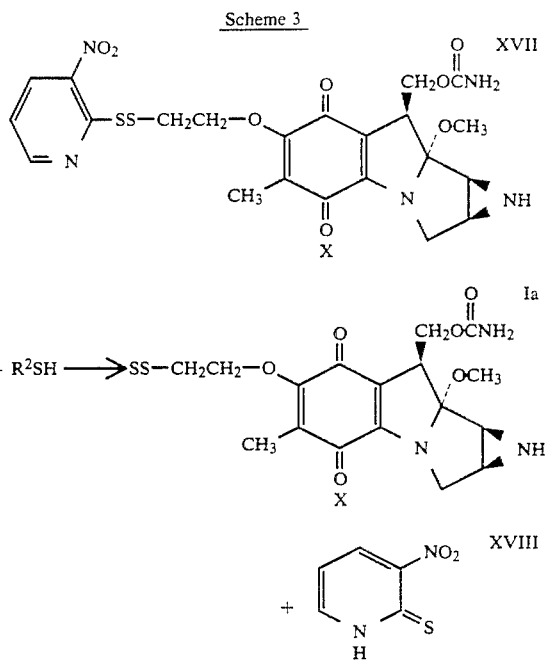

Alternatively, if it is desired to prepare mitosanes of Formula II or III wherein $Alk_2$ is other than ethylene, such as trimethylene or propylene, then the appropriate triazene of Formula V or VI is utilized in the procedure depicted in Scheme 2 to produce disulfide mitosanes having the Formula Ib

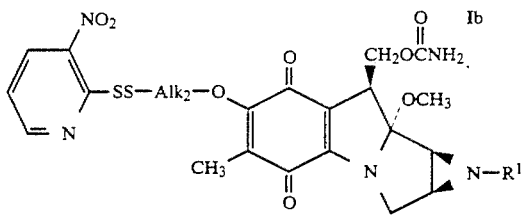

wherein $Alk_2$ and $R^1$ are as defined above.

There are two general synthetic procedures described herein for the preparation of lipophilic as well as hydrophilic mitosanes of the Formula Ia. General procedure A is employed for preparing either lipophilic or moderately soluble disulfides of Formula Ia, whereas general procedure B is employed for water-soluble disulfides of Formula Ia which are preferably isolated as sodium salts or as zwitterionic forms. Preferably, at least one equivalent of the mercaptan $R^2SH$ per equivalent of mitosane of Formula XVII is employed, and the reaction may be carried out in the presence of about one equivalent of base per equivalent of mercaptan $R^2SH$. Preferred bases are the tertiary amines, e.g. triethylmaine, N-methylmorpholine, N-methylpiperidine, pyridine, 2,6-lutidine and the inorganic bases, e.g. sodium bicarbonate, potassium carbonate, potassium bicarbonate and the like. Suitable inert solvents for the reaction of starting materials of Formula XVII and $R^2SH$ are the lower alkanols, lower alkanoic lower alkyl esters, lower aliphatic ketones, the cyclic aliphatic ethers, the lower polyhalogenated aliphatic hydrocarbons and water.

The organic solvents contain up to 8 carbon atoms, but those boiling at temperatures of less than 100° C. are preferred. Specific preferred solvents are methylene chloride, methanol, acetone, water and mixtures thereof. The reaction may be carried out at the reflux temperature of the reaction mixture or up to about 60° C. It is preferred to carry out the reaction at room temperature or below, for instance within the range of 0° C. to 25° C.

The foregoing reaction conditions and precautions are generally applicable to the preparation of other disulfide mitosanes of Formulas Ia and Ib according to the general procedure depicted in Scheme 3.

The following is an enumeration of representative thiols of the Formula $R^3Alk_1SH$ or $R^4SH$ which may be converted via reaction with the Bunte salt XV or sulfenylthiocarbonate XVI to produce intermediates Formulas XIII and XIV, which in turn are converted to products of the present invention as described. In the case of the preferred embodiment, the representative thiols may be employed in a reaction with mitosanes of Formula Ia or Ib to produce products of the present invention. However, the only limitations to the methodology of the present invention is the use of thiols containing terminal primary alkyl amines which may lead to a mixture of products and the use of heteroaromatic thiols which may not react with compounds of the Formula Ia or Ib.

HSCH₃
HSCH₂CH₃
HSCH₂CH₂CH₃
HSCH(CH₃)₂
HS(CH₂)₃CH₃

HS—CH—CH₂CH₃
       |
       CH₃

HSCH₂CH(CH₃)₂

CH₃
       |
HS—C—CH₃
       |
       CH₃

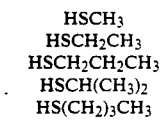

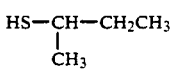

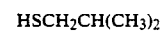

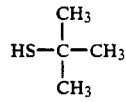

-continued

HS—CH₂—CH=CH₂
HS—CH₂—CH=C(CH₃)₂
HS—CH₂—C≡CH
HS—CH₂—C≡C—CH₃

$HS(CH_2)_nOR^1$  n = 2-4; $R^1$ = H, $\overset{O}{\underset{\parallel}{C}}CH_3$, CH₃

$HS(CH_2)_n\overset{O}{\underset{\parallel}{C}}XR$  n = 1-3; X = O, NH, $NR^1$; $R/R^1$ = H, CH₃

$HS(CH_2)_nNHR^1$  n = 2-4;  $R^1$ = CH₃, CH₂CH₃, CH₂CH₂CH₃, $\overset{O}{\underset{\parallel}{C}}CH_3$ $HS(CH_2)_nNR^1R^2$  n = 2-4; $R^1/R^2$ = CH₃, CH₂CH₃
HS—CH₂CH₂SCH₃
HS—CH₂CH₂NHC(CH₃)₃

CH₃
       |
HS—CH₂—C—CH₂NHR¹  $R^1$ = CH₃, $\overset{O}{\underset{\parallel}{C}}CH_3$
       |
       CH₃

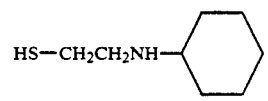

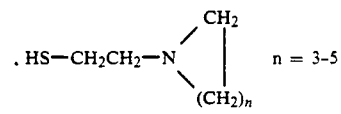

CH₂NR¹R²
       |
HS—CH—CH₂NR¹R²  $R^1$ = CH₃; $R^2$ = H, CH₃

HS—CH₂—CH—CH₂NHR¹  $R^1$ = CH₃
              |
              NHR¹

HS—CH₂—CH—NH₂  + peptides
          |
          CO₂H

HS—CH₂—CH—CH₂—NH₂  + peptides
          |
          CO₂H

HS—CH₂—CH—CH₂—CO₂H  +peptides
          |
          NH₂

CH₂CO₂H
       |
HS—CH₂CH₂CH  + peptides
       |
       NH₂

NH₂
                    |
       NHCOCH₂CH₂CHCO₂H
       |
HS—CH₂CH
       |
       CONHCH₂CO₂H

HS—CH=CH—NH$\overset{O}{\underset{\parallel}{C}}$CH₃ .

-continued

HS—CH₂—CH—CH₂OH
           |
           OH

CH₃
       |
HS—CH₂CH—CH₂OH

HS—CH₂CH—CH₂NR¹R²    R¹ = CH₃; R² = H, CH₃
       |
       OCH₃

HS—CH₂CH₂—N—CH₃
           |
           OCH₃

HS—CH₂CH₂NH—C₆H₅

HS—CH₂CH₂NH—(2-pyridyl)

HS—CH₂CH₂—NH—(2-thiazolyl)

CH₃
           |
HS—CH₂CH₂—O—C—CH₃
           |
           CH₃

HS—C₆H₅

HS—C₆H₄—N(CH₃)₂

HS—C₆H₄—OCH₃

HS—C₆H₄—NHCH₃

HS—C₆H₄—NHC(O)CH₃

HS—C₆H₃(CO₂H)(NH₂)

-continued

HS—(3-pyridyl)

HS—(2-quinolyl)

HS—(2-furyl)

HS—(3-pyridyl with 2-N(CH₃)₂)

HS—CH₂—C₆H₅

HS—CH₂—CH=CH—C₆H₅

HS—CH₂CH₂—C₆H₄—NHC(O)CH₃

HS—(CH₂)ₙ—(2-pyridyl)    n = 1, 2

HS—(CH₂)ₙ—(3-pyridyl)    n = 1, 2

HS—(CH₂)ₙ—(4-pyridyl)    n = 1, 2

HS—(CH₂)ₙ—(1,2,4-triazolyl)    n = 2, 4

HS—(CH₂)ₙ—(1,2,3-triazolyl, R¹)    n = 2-4; R¹ = OCH₂CH₃

HS—(CH₂)ₙ—(2-imidazolyl)    n = 1, 2

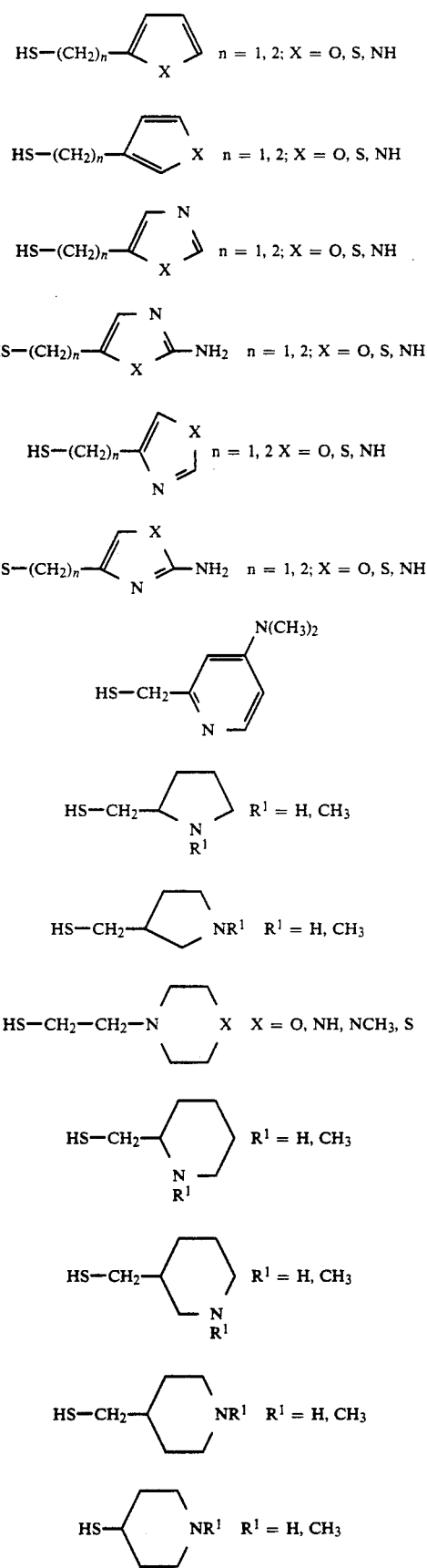

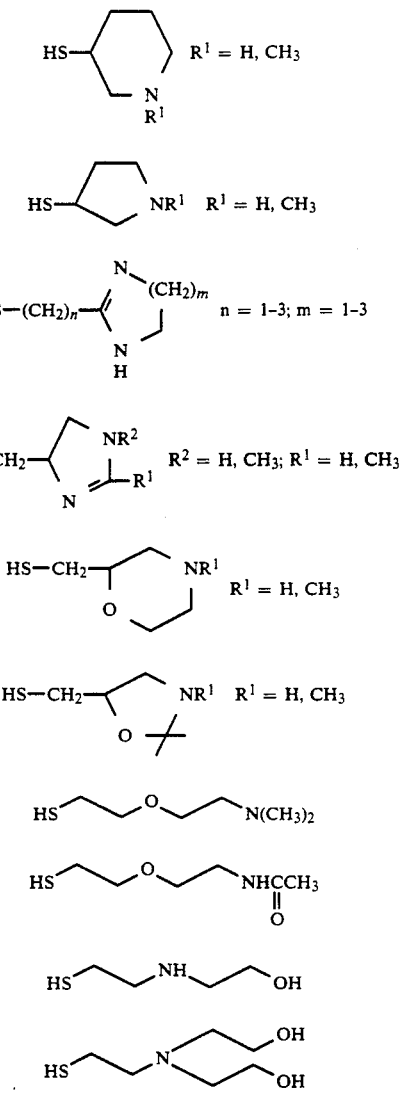

Usefulness of compounds of Formulas I and IX in the antineoplastic therapeutic methods of the invention is demonstrated by the results of in vivo screening procedures wherein the compounds are administered in varying dosage amounts to mice in which a P-388 leukemic or B16 melanomic condition is induced.

Compounds according to the present invention are believed to possess anti-bacterial activity against gram-positive and gram-negative microorganisms in a manner similar to that observed for the naturally occurring mitomycins and are thus potentially useful as therapeutic agents in treating bacterial infections in humans and animals.

Activity Against P-388 Murine Leukemia

Table I contains the results of laboratory tests with $CDF_1$ mice implanted intraperitoneally with a tumor inoculum of $10^6$ ascites cells of P-388 murine leukemia and treated with various doses of either a test compound of Formula I or II, or with mitomycin C. The compounds were administered by intraperitoneal injection. Groups of six mice were used for each dosage amount and they were treated with a single dose of the compound on the day after inoculation. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. The "maximum effect" in the following Table is expressed as % T/C and the dose giving that effect is given. The values in parenthesis are the values obtained with mitomycin C as the positive control of the present substances to mitomycin C can be estimated. A minimum effect in terms of % T/C was considered to be 125. The minimum effective dose reported in the following Table is that dose giving a % T/C of approximately 125. The two values given in each instance in the "average weight change" column are respectively the average weight change per mouse at the maximum effective dose and at the minimum effective dose.

TABLE I

Inhibition of P-388 Murine Leukemia

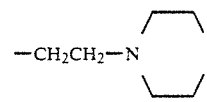

| Compound of Example No. | R | Maximum Effect % T/C | Maximum Effect Dose[1] | Minimum Effect Dose[1] | Average Wt. Change[2] |
|---|---|---|---|---|---|
| 12[3] | n-Bu | 167(306)[4] | 1.6(3.2)[4] | 0.2 | +0.1; −0.4 |
| 13[3] | i-Pr | 167(306) | 1.6(3.2) | 0.05 | −0.7; +0.1 |
| 14 | 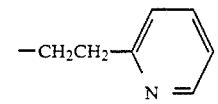 | 222(306) | 6.4(3.2) | <0.05 | −1.7; −0.5 |
| 15 | 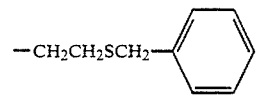 | 233(306) | 3.2(3.2) | <0.05 | −2.4; +0.2 |
| 16 | 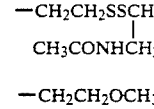 | 156(306) | 6.4(3.2) | 0.2 | −0.7; +0.3 |
| 17 | —CH$_2$CH$_2$SSCH$_2$<br>               \|<br>        CH$_3$CONHCH$_2$ | 183(306) | 6.4(3.2) | 0.1 | −1.2; −0.3 |
| 18[3] | —CH$_2$CH$_2$OCH$_3$ | 211(172) | 0.4(3.2) | <0.05 | −0.6; +1.3 |
| 19 | 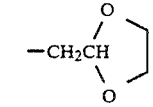 | 267(172) | 0.4(3.2) | <0.05 | +0.9; +1.7 |
| 20 | 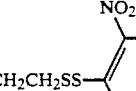 | 206(>333) | 6.4(4.8) | 0.2 | −1.0; +1.5 |
| 26 | 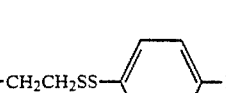 | 178(>333) | 12.8(4.8) | 0.2 | +0.4; +2.1 |

TABLE I-continued

Inhibition of P-388 Murine Leukemia

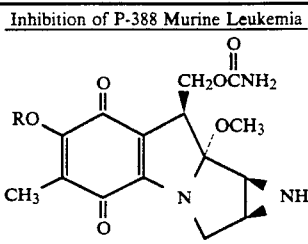

| Compound of Example No. | R | Maximum Effect %T/C | Dose[1] | Minimum Effect Dose[1] | Average Wt. Change[2] |
|---|---|---|---|---|---|
| 28 |  | 194(>333) | 3.2(4.8) | <0.1 | −3.1; +1.8 |

[1]mg/kg of body weight
[2]average grams per day for each maximal and minimal effective doses
[3]Urakawa et al., J. Antibiotics, 23, 804–809 (1980)
[4]values in parentheses are for mitomycin C tested in the same run

Activity Against B16 Melanoma

Table II contains results of antitumor tests using the B16 malanoma grown in mice. BDF$_1$ mice were employed and inoculated subcutaneously with the tumor implant. A 60-day protocol was used. Groups of ten mice were used for each dosage amount tested, and the mean surfavial time for each group was determined. Control animals inoculated in the same way as the test animals and treated with the injection vehicle and no drug exhibited a mean survival time of 24 days. The survival time relative to that of the controls (* T/C) was used as a measure of effectiveness, and the maximal effective dose and minimal effective dose for each test compound was determined. The minimal effective dose was defined as thereat dose exhibiting a % T/C value of 125. For each dosage level, the test animals were treated with the test compound on days 1, 5 and 9 by the intravenous route.

TABLE II

| | B16 Melanoma | | | |
|---|---|---|---|---|
| Compound of Example No. | Maximum Effect %T/C | Dose[1] | Minimum Effective Dose[1] | Average Wt. Change[2] |
| 28 | 167 (112)[3] | 1.6 (3)[3] | <0.4 | −0.9; +1.4 |
|  | >214 (145) | 2.4 (3) | <1.6 | −2.4; −1.9 |
| 20 | 110 (112) | 3.2 (3) | 3.2 | +0.5; +0.5 |
| 26 | 152 (145) | 1.6 (3) | <1.6 | −0.6; −0.6 |

[1]mg/kg of body weight
[2]average grams per day for each maximal and minimal effective dose
[3]values in parentheses are for mitomycin C tested in the same run In view of the antitumor activity observed in experimental animal tumors, the invention includes use of the substances of the present invention for inhibiting mammalian tumors. For this purpose, they are administered systematically to a mammal bearing a tumor in substantially nontoxic antitumor effective dose.

The compounds of the present invention are intended primarily for use by injection in much the same way and for some of the same purposes as mitomycin C. Somewhat larger or smaller doses may be employed depending upon the particular tumor sensitivity. They are readily distributed as dry pharmaceutical compositions containing diluents, buffers, stabilizers, solubilizers and ingredients contributing to pharmaceutical elegance. These compositions are then constituted with an injectable liquid medium extemporaneously just prior to use. Suitable injectable liquids include water, isotonic saline and the like.

DESCRIPTION OF SPECIFIC EMBODIMENTS

In the following procedures and examples, all temperatures are given in degrees Centigrade, and melting points are uncorrected. Proton nuclear magnetic resonance ($^1$H NMR) spectra were recorded on a Varian XL100, Joel FX-90Q or Bruker WM 360 spectrometer in either pyridine-d$_5$ or D$_2$O as indicated. When pyridine-d$_5$ is used as the solvent, the pyridine resonance at $\delta = 8.57$ is used as an internal reference, whereas with D$_2$O as solvent TSP is used as the internal reference. Chemical shifts are reported in $\delta$ units and coupling constants in Hertz. Splitting patterns are designated as follows: s, singlet; d, doublet; t, triplet; q, quartet; m, multiplet; bs, broad signal; dd, doublet of doublet; dt, doublet of triplet. Infrared spectra were determined either on a Beckman Model 4240 spectrometer or a Nicolet 5DX FT-IR spectrometer and are reported in reciprocal centixeters. Ultraviolet (UV) spectra were determined either on a Cary Model 290 spectrometer or a Hewlitt Packard 8450A spectrometer equipped with a multidiode array detector. Thin layer chromatography (TLC) was carried out on 0.25 mm Analtech silica gel GF plates. Flash chromatography was run with either Woelm neutral alumina (DCC grade) or Woelm silica gel (32–63μm) and the indicated solvents. All evaporations of solvents were performed under reduced pressure and below 40° C.

The 1-alkyl-3-aryltriazenes make up a class of reagents which are known to be useful for reacting with carboxylic acids to form the corresponding lower alkyl esters. 1-Methyl-3-(4-methylphenyl)triazene may be prepared as follows:

PROCEDURE 1

E. H. White et al., Org. Syn., 48, 102–195 (1968).

1-Methyl-3-p-tolyltriazene. p-Toluidine (50.2 g, 0.47 mole) is added to a 2-l flask equipped with a 200-ml dropping funnel and an efficient stirrer, and the flask is immersed in an ice-salt bath at ca. −10°. A solution of 46.8 g (0.55 mole) of potassium nitrite in 150 ml of water is placed in the dropping funnel, and a mixture of 250 g of crushed ice and 140 ml of concentrated hydrochloric acid is added to the p-toluidine with stirring. The potassium nitrite solution is slowly added with continued stirring during 1-2 hours until a positive starch-potassium iodide test is obtained (Note 1), and the mixture is stirred for an additional hour to ensure the reaction of all the toluidine.

The solution of p-toluenediazonium chloride is then brought to pH 6.8-7.2 at 0° with cold, concentrated, aqueous sodium carbonate, whereupon the solution becomes red to orange in color and a small amount of red material settles out. The cold, neutral solution is transferred to a dropping funnel and added slowly to a vigorously stirred mixture of 150 g of sodium carbonate, 300 ml of 30%-35% aqueous methylamine (Note 2), and 100 g of crushed ice in a 3-1 flask. The reaction mixture is kept at ca. −10° during the addition, which requires about 45 minutes (Note 3). The solution is extracted with three 1-1 portions of ether. The ethereal extracts are dried with anhydrous sodium sulfate and evaporated on a rotary evaporator at room temperature to give 65 g of crude 1-methyl-3-p-tolyltriazene (Note 4). This is placed in a water-cooled sublimer, and the triazene is sublimed at 50° (1 mm.); 43.3 g (0.29 mole, 62%) of a yellow, crystalline sublimate, m.p. 77°-80°, is obtained (Note 5). The sublimate can be recrystallized from hexane to give the triazene as white needles, m.p. 80.5°-81.5°. More conveniently, it is dissolved in the minimum amount of ether, and the solution is diluted with 2 volumes of hexane and cooled to 0° to give flat plates with a slightly yellow cast; m.p. 79°-81°. The yield of pure triazene is 33-37 g (47%-53%) (Note 6).

NOTES

1. The individual tests with starch-potassium iodide paper should be made 1-2 minutes after the addition of potassium nitrite has been stopped.

2. 40% aqueous methylamine may be substituted.

3. The reaction is over when a drop of solution no longer gives a red color with a solution of β-naphthol in aqueous sodium carbonate.

4. The chief impurity is 1,5-di-p-tolyl-3-methyl-1,4,-pentazadiene (m.p. 148°). This can be removed by fractional crystallization, but it is easier to sublime the triazene from the reaction mixture.

5. The sublimate contains a trace of 1,3-di-p-tolyl-triazene, as shown by thin-layer chromatography. Recrystallization yields the pure 1-methyl-3-p-tolyltriazene.

6. This procedure works well only with water-soluble amines. Procedure 2 given below is more suitable for the preparation of triazenes of water-insoluble amines.

PROCEDURE 2

E. H. White et al., *Tetrahederon Letters No.* 21, p. 761 (1961).

1-n-Butyl-3-p-chlorophenyltriazene. A solution of p-chlorobenzenediazonium hexafluorophosphate (recrystallized from acetone-xethanol) (2.87 g, 10.1 mmoles) in dimethylformamide (dimethylamine-free) was added slowly to a stirred mixture of n-butylamine (0.73 g, 10.0 mmoles), powdered sodium carbonate (15 g), and dimethylformamide (30 ml) stirred and maintained at −5°. The diazonium salt solution may be used at room temperature; however, a purer product is usually obtained if the diazonium salt solution is prepared in and delivered from a cooled separatory funnel maintained at ca. −50°. The mixture was warmed to 0° and stirred until a negative test was obtained with 2-naphthol (only a few minutes are usually required). Ether was added, the mixture was filtered, and the filtrate was washed thoroughly with water, then dried. (The triazene may be isolated at this point and recrystallized from pentane at low temperatures.

PROCEDURE 3

7-Hydroxy-9a-methoxymitosane. Mitomycin C (2.2 g, 6.6 mmoles) was dissolved in 140 ml 0.1 N methanolic NaOH (50%) and the reaction mixture was stirred at room temperature for 30 hours. The solution was then adjusted to ca. pH 4.0 with 1N HCl and extracted with ethyl (4×500 ml). The combined ethyl acetate extracts were dried ($Na_2SO_4$) and evaporated under reduced pressure at about 30° C. to 35° C. to obtain a solid residue, which upon dissolving in ether and treating with excess hexane afforded a purple precipitate. The precipitate was collected and air dried to afford the title compound as a fine purple powder (1.4 g, 63%).

$^1$H NMR (pyridine-$d_5$, δ): 2.05(s, 3H), 2.14(bs, 1H), 2.74(bs, 1H), 3.13(d, 1H), 3.24(s, 3H), 3.56(d, 1H), 4.00(dd, 1H), 4.37(d, 1H), 5.05(t, 1H), 5.40(dd, 1H), 5.90(bs, 2H).

PROCEDURE 4

Mitomycin A. A 100 mg (0.30 mmole) quantity of 7-hydroxy9a-methoxymitosane and 100 mg (0.67 mmole) quantity of 3-methyl-1-p-tolyltriazene was dissolved in 2 ml methylene chloride and 10 ml diethyl ether. The solution, after gently refluxing for 6 hours was stirred at room temperature for 18 hours. TLC [methylene chloride:methanol (90:10)] revealed the appearance of a deep purple spot at $R_f$=0.36 with a trace amount of impurity at $R_f$=0.41. The reaction mixture was concentrated to dryness and chromatographed on Woelm neutral alumina employing methylene chloride and methylene chloride:methanol (30:1) as eluting solvents. Fractions containing the component at $R_f$=0.36 were pooled and concentrated to dryness. Precipitation of the dry residue from methylene chloride and hexane afforded the title compound as a fine amorphous purple powder (25 mg, 24%), mp 161°.

Anal. Calc'd for $C_{16}H_{19}N_3O_6$: C, 54.96; H, 5.44; N, 12.02; Found: C, 53.96; H, 5.37; N, 11.99.

IR(KBr), max, cm$^{-1}$: 3400, 3300, 2950, 1700, 1630, 1575, 1200, 1060.

1H NMR (pyridine-$d_5$, δ): 1.82(s, 3H), 2.74(dd, 1H), 3.12(d, 1H), 3.24(s, 3H), 3.54(dd, 1H), 3.96(dd, 1H), 4.02(s, 3H), 4.22(d, 1H), 4.84(bs, 2H), 5.02(t, 1H), 5.38(dd, 1H).

The yield in procedure 4 is raised to 63% by employing methylene chloride as reaction solvent and room temperature for a 24 hour period.

PROCEDURE 5

In a 250 ml one neck round bottom flask was placed solid $Na_2CO_3$, 35% aqueous solution of amine (amount is in Procedure 1) and ice, and the suspension was stirred at −5° C. (ice-salt bath). To this suspension was added dropwise, a cold suspension of p-chlorobenzenediazonium hexafluorophosphate (Aldrich Chemical Co.) in ice, water, $Na_2CO_3$ (solution about pH 7). After the addition was complete, the reaction mixture was extracted with diethyl ether. The combined diethyl ether extract was backwashed with water, dried ($Na_2SO_4$) and concentrated. The yellowish solid residue was purified by column chromatography over Woelm alumina using hexane-xethylene chloride (1:1) as eluting solvent ($^1$H NMR recorded).

EXAMPLES 1-10

The triazenes 1-7 of Table III which follows were prepared according to general Procedure 1 described above wherein the triazene of Example 1 is exemplified. The triazenes were purified by column chromatography on Woelm alumina.

The triazenes 8-10 of Table III were prepared according to general Procedure 5 described above.

procedure. A solution containing 21.15 mmoles of the diazonium salt in 45 ml of solution was prepared in this fashion and placed in a dropping funnel connected to a 250 ml 3 neck, round bottom flask containing 5.34 g (20.0 mmoles) of 2-(3-nitro-2-pyridyldithio) ethylamine, 7 g of sodium carbonate, and 150 ml of dioxane which had been added to the flask in that sequence. Saturated aqueous sodium carbonate solution, 6 ml, and 10 g of ice were added to the flask. The flask was chilled in an ice bath and the contents stirred mechanically. The diazonium salt solution was then added dropwise during a

TABLE III

Triazenes $$RNH_2 + X-\bigcirc-N_2^{\oplus}A^{\ominus} \longrightarrow X-\bigcirc-N=N-NHR$$

| Example No. | Amine | Diazonium Salt | Triazene |
|---|---|---|---|
| 1 | $CH_3NH_2$ | $CH_3-\bigcirc-N_2^+Cl^-$ | p-$CH_3C_6H_4N=N-NHCH_3$ |
| 2 | $CH_3(CH_2)_3NH_2$ | " | p-$CH_3C_6H_4N=N-\overset{H}{\underset{|}{N}}(CH_2)_3CH_3$ |
| 3 | $(CH_3)_2CHNH_2$ | " | p-$CH_3C_6H_4N=N-NHCH(CH_3)_2$ |
| 4 | $O\diagdown N-CH_2CH_2NH_2$ | " | p-$CH_3C_6H_4N=N-NHCH_2CH_2N\diagdown O$ |
| 5 | pyridyl-$CH_2CH_2NH_2$ | " | p-$CH_3C_6H_4N=N-NHCH_2CH_2$-pyridyl |
| 6 | phenyl-$CH_2SCH_2CH_2NH_2$ | " | p-$CH_3C_6H_4N=N-NHCH_2CH_2SCH_2$-phenyl |
| 7 | $CH_3OCNHCH_2CH_2SSCH_2CH_2NH_2$ | " | p-$CH_3C_6H_4N=N-NHCH_2CH_2SSCH_2CH_2NHCOCH_3$ |
| 8 | $CH_3OCH_2CH_2NH_2$ | $Cl-\bigcirc-N_2^+PF_6^-$ | p-$ClC_6H_4N=N-NHCH_2CH_2OCH_3$ |
| 9 | dioxolanyl-$CH_2NH_2$ | " | p-$ClC_6H_4N=N-NHCH_2CH$-dioxolanyl |
| 10 | tetrahydrofuranyl-$CH_2NH_2$ | " | p-$ClC_6H_4N=N-NH-CH_2$-tetrahydrofuranyl |

EXAMPLE 11

1-[2-(3-Nitro-2-pyridyldithio)ethyl]-3-(4-methylphenyl)-triazene

A solution of 4-methylphenyldiazonium chloride is prepared as described in Procedure 1 from p-toluidine and adjusted to pH 6.8-7.2 at 0° C. as described in that one hour period from the dropping funnel. When addition had been completed the reaction mixture was allowed to warm to room temperature and was then extracted with three 400 ml portions of ether. Drying and evaporation of the extracts yielded the desired product which was purified by chromatography using an alumina packed column, one inch in diameter and ten inches long, using hexane:methylene chloride (4:1); hexane:methylene chloride (3:2); hexane:methylene chloride (1:4); and finally xethylene chloride containing 1% methanol for development and elution of the column. The appropriate fractions (identified by TLC) were combined and evaporated to yield 2.5 g of the title compound.

EXAMPLES 12-19

General procedure for preparing 7-alkoxy-9a-methoxymitosanes (12-19)

A solution of triazene (2.4 equivalents) in $CH_2Cl_2$:methanol (4:1) was added to a solution of 7-hydroxy-9a-methoxymitosane (prepared in Procedure 3) in $CH_2Cl_2$:methanol (4:1). The reaction mixture was stirred at room temperature and the progress of the reaction was monitored by thin layer chromatography (TLC) (10% MeOH in $CH_2Cl_2$). The 7-alkoxy-9a-methoxymitosane product appears as a dark purple spot on the TLC. The reaction mixture is chromatographed on Woelm alumina when the reaction is judged to be complete on the basis of the TLC, and the 7-alkoxy-9a-methoxymitosane is obtained as an amorphous solid. The products produced are identified as Example Nos. 12-19 in Table IV.

TABLE IV

7-Alkoxy-9a-methoxymitosanes

| Example No. | Formula | $^1$H NMR (Pyridine-$d_5$, δ) ppm | IR (cm$^-$) | Elemental Analysis[a] |
|---|---|---|---|---|
| 12[b] | R = —CH$_2$CH$_2$CH$_2$CH$_3$ | 0.80(t, 3H), 1.44(m, 4H), 1.84(s, 3H), 2.08(bs, 1H), 2.72(bs, 1H), 3.08(bs, 1H), 3.20(s, 3H), 3.52(d, 1H), 4.00(dd, 1H), 4.28(m, 3H), 5.04(t, 1H), 5.44(dd, 1H), 7.64(bs, 2H). | — | T: C, 58.30; H, 6.44; N, 10.74<br>F: C, 58.34; H, 6.25; N, 10.80 |
| 13[b] | R = —CH(CH$_3$)$_2$ | 1.20(d, 3H), 1.28(d, 3H), 1.88(s, 3H), 2.20(bs, 1H), 2.76(bs, 1H), 3.16(bs, 1H), 3.24(s, 3H), 3.56(d, 1H), 4.00(dd, 1H), 4.24(d, 1H), 5.00(m, 2H), 5.44(dd, 1H). | — | — |
| 14[c,d] | R = —CH$_2$CH$_2$—N(morpholine)O | 1.96(s, 3H), 2.40(m, 4H), 2.56(t, 2H), 2.76(bs, 1H), 3.16(d, 1H), 3.24(s, 3H), 3.54(d, 1H), 3.68(m, 4H), 4.00(dd, 1H), 4.26(d, 1H), 4.60(m, 2H), 5.04(t, 1H), 5.44(dd, 1H). | 3480, 3260, 2940, 1725, 1630, 1210, 1055 | T: C, 52.60; H, 5.95; N, 11.41<br>F: C, 52.75; H, 6.00; N, 11.44<br>(Corrected for 0.5 mole % of CH$_2$Cl$_2$). |
| 15 | R = —CH$_2$CH$_2$-(pyridyl) | 1.68(s, 3H), 1.96(bs, 1H), 2.72(bs, 1H), 3.08(bs, 1H), 3.20(t, 2H), 3.20(t, 3H), 3.50(d, 1H), 3.92(dd, 1H), 4.16(d, 1H), 4.92(m), 5.36(dd, 1H). | 3430, 3300, 2930, 1715, 1625, 1210, 1060 | T: C, 59.99, H, 5.49; N, 12.72<br>F: C, 59.94; H, 5.66; N, 12.63 |
| 16 | R = —CH$_2$CH$_2$SCH$_2$-(phenyl) | 1.92(s, 3H), 2.12(bs, 1H), 2.76(bs, 1H), 2.84(t, 2H), 3.16(bs, 1H), 3.26(s, 3H), 3.56(d, 1H), 3.86(s, 2H), 4.04(dd, 1H), 4.28(d, 1H), 4.60(m, 2H), 5.12(t, 1H), 5.48(dd, 1H), 7.46(m), 7.76(bs). | 3420, 3280, 2930, 1895, 1620, 1210, 1065 | T: C, 59.37; H, 5.60; N, 8.65<br>S, 6.60<br>F: C, 59.26; H, 5.66; N, 8.63, S, 6.66 |
| 17 | R = —CH$_2$CH$_2$SS—CH$_2$CH$_2$NHCOCH$_3$ | 1.88(s, 3H), 2.04(s, 3H), 2.24(bs, 1H), 2.76(bs, 1H), 3.08(m, 5H), 3.24(s, 3H), 3.52(d, 1H), 3.76(t, 2H), 3.98(dd, 1H), 4.24(d, 1H), 4.72(t, 2H), 5.04(t, 1H), 5.40(dd, 1H). | 3300, 2920, 1710, 1625, 1210, 1065 | — |
| 18[b] | R = —CH$_2$CH$_2$OCH$_3$ | 1.88(s, 3H), 2.00(bs, 1H), 2.72(bs, 1H), 3.08(d, 1H), 3.20(s, 3H), 3.24(s, 3H), 3.52(m, 3H), 3.96(dd, 1H), 4.20(d, 1H), 4.56(m, 2H), 5.04(t, 1H), 5.40(dd, 1H). | 3440, 3280, 2950, 1700, 1630, 1200, 1065 | T: C, 54.96; H, 5.89; N, 10.68<br>F: C, 54.45; H, 5.85; N, 10.42 |

TABLE IV-continued

7-Alkoxy-9a-methoxymitosanes

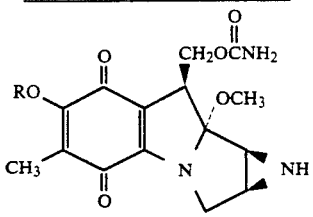

| Example No. | Formula | $^1$H NMR (Pyridine-$d_5$, δ) ppm | IR (cm$^-$) | Elemental Analysis[a] |
|---|---|---|---|---|
| 19 | R = —CH$_2$—CH(–O–O–) (epoxide/dioxolane ring) | 1.92(s, 3H), 2.72(m, 1H), 3.08(d, 1H), 3.20(s, 3H), 3.52(dd, 1H), 3.84(m, 4H), 3.94(dd, 1H), 4.20(d, 1H), 4.60(m, 2H), 4.96(t, 1H), 5.28(m, 1H), 5.36(dd, 1H), 7.52(bs, 2H). | 3460, 3360, 3200, 2960, 1720, 1625, 1210, 1060 | T: C, 54.15; H, 5.50; N, 9.97 F: C, 53.44; H, 5.46; N, 9.74 |

[a]T = theory, F = found
[b]Urakawa et al., J. Antibiotics, 23, 804–809 (1980)
[c]Molecular ion observed in (+) and (−) CIMS
[d]Also preparable by alcoholysis of mitomycin A, Urakawa et al., loc. cit.

EXAMPLE 20

9a-Methoxy-7-]2-(3-nitro-2-pyridyldithio)ethoxy]mitosane (20)

7-Hydroxy-9a-methoxymitosane. 580 mg (1.73 mmoles) is placed in a round bottom flask and dissolved in 60 ml of methylene chloride. The triazene of Example 11, approximately 2.5 g (5.7 mmoles) wa added to the solution in the flask and the mixture was stirred at 5° C. for 14 hours and then at room temperature for 8 hours. The progress of the reaction was monitored by silica TLC using methylene chloride:methanol (9:1). The reaction was kept at room temperature for an additional 26 hours and then worked up by column chromatography on column ⅜ of an inch wide by 12 inches long packed with alumina. The solvents employed in sequence for development and elution were 200 ml portions each of methylene chloride; 0.5% methanol in methylene chloride; 1.0% methanol in methylene chloride; 1.5% methanol in methylene chloride; 2% methanol in methylene chloride; and 4% methanol in methylene chloride. The appropriate fractions were combined and evaporated to yield the title compound, 470 mg.

Anal. Calc'd for $C_{22}H_{23}N_5O_8S_2$: C, 45.65; H, 4.09; N, 11.82 (corrected for 0.5mole % of $CH_2Cl_2$): Found: C, 45.74; H, 4.14; N, 11.61.

IR(KBr), $\tilde{\nu}$max, cm$^{-1}$: 3440–3200, 3060, 2930, 1720, 1570, 1510, 1395, 1335, 1210, 1055.

$^1$H NMR (pyridine-d5, δ): 1.81(s, 3H), 2.00(bs, 1H), 2.61(bs, 1H), 2.98(bs, 1H), 3.08(s, 3H), 3.20(m, 2H), 3.39(d, 1H), 3.83(dd, 1H), 4.07(d, 1H), 4.59–4.89(m, 3H), 5.21(dd, 1H), 7.16(dd, 1H), 8.31(dd, 1H), 8.71(dd, 1H).

By adaptation of the procedure of Examples 11 and 20 to other ω-(3-nitro-2-pyridyldithio)alkyl amines having 2 to 6 carbon atoms in the alkyl group, mitosane derivatives of the following formula may be prepared.

n = 2–6
R$^1$ = H, or C$_{1-6}$ alkyl n = 2–6
R$^1$ = H, or C$_{1-6}$ alkyl

EXAMPLES 21–34

The 7-alkoxydithio-9a-methoxymitosanes 21–34 of Table V which follows were prepared according to general Procedure A or B described below and indicated in Table V. The physical data for the mitosane compounds 21–34 are reported in Table VI which also follows.

PROCEDURE A

To a deoxygenated solution of mitosane of Example 20 (~0.1 mmole) in acetone (3–5 ml) is added with stirring, under argon, triethylamine (~1.1 equivalents) followed by dropwise or portion wise addition of a mercaptan[a] (1 equivalent) in acetone (1–2 ml). In most of the reactions[b], the progress of the reaction is monitored by silica gel thin layer chromatography (10% CH$_3$OH in CH$_2$Cl$_2$). The completion of reaction is signaled by the disappearance of spot corresponding to the starting material and appearance of the product spot. At this point the reaction mixture is concentrated under reduced pressure (at ~30° C.) and the residue chromatographed on a neutral Woelm alumina column (¼"×10") slurry packed with 2%–5% CH$_3$OH in CH$_2$Cl$_2$. This procedure separates the desired mitosane product from the pyridyl thione by-product, which is retained on the column. The product thus eluted using 2%–5% CH$_3$OH in CH$_2$Cl$_2$ is further carefully purified by flash silica gel chromatography using 5%–7%

CH₃OH in CH₂Cl₂ as the eluting solvent. The major band corresponding to product is isolated and the amorphous 7-alkoxydithio-9a-methoxymitosane is characterized.

a) In cases were starting mercaptan is impure >1 equivalent of thiol is required. b) In cases where the starting mitosane of Example 20 and the product have very close $R_f$ values on TLC, a high pressure liquid chromatography (HPLC) monitoring (μBondapak-C₁₈ column) is employed.

PROCEDURE B

To a solution of mitosane of Example 20 (~0.1 mmole) in 2%-5% acetone[a] in methanol (10 ml) is added saturated aqueous NaHCO₃ solution[b] (~6 drops), followed by addition of mercaptan (1 equivalent) in methanol[c] (1 ml). The progress of the reaction is monitored by TLC (silica gel, 10% CH₃OH in CH₂Cl₂). At the comletion of reaction, the reaction mixture is diluted with water (15 ml) and concentrated to about 10 ml under reduced pressure at about 30° C. The resulting solution is chromatographed on a reverse phase C-18 column with stepwise gradient elution (100%[d] H₂O to 80% CH₃OH in H₂O). The product, eluting as a major red band, is collected and concentrated to yield the 7-alkoxydithio-9a-methoxymitosane as an amorphous solid. If further purification is needed, the above chromatography step is repeated.

a) Methylene chloride can also be used, but acetone is preferred. b) In the case where the mercaptan is L-cystiene, this base is not employed. c) Water is employed if the starting thiol is water soluble. d) Elution with water separates the yellow pyridyl thione byproduct from the product, which is retained on the column.

TABLE V

7-Alkoxydithio-9a-methoxymitosanes

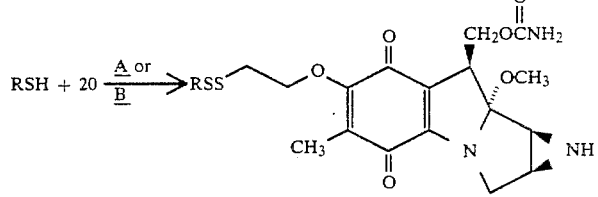

| Example No. | Thiol (RSH) | Procedure | Product |
|---|---|---|---|
| 21 | ethyl 2-mercaptoacetate | A | R = —CH₂CH₂OC(O)CH₃ |
| 22 | 3-mercapto-1,2-propanediol | A | R = —CH₂CH(OH)CH₂OH |
| 23 | 3-mercaptopropionic acid | B | R = —CH₂CH₂COO⁻Na⁺ |
| 24 | cysteine | B | R = —CH₂CH(NH₃⁺)COO⁻ |
| 25 | thiophenol | A | 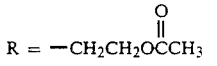 |
| 26 | p-nitrobenzenethiol | A | 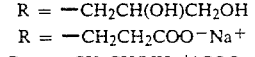 |
| 27 | p-methoxybenzenethiol | A | 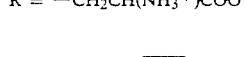 |
| 28 | p-aminobenzenethiol | A | 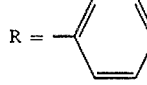 |
| 29 | 2-mercaptobenzoic acid | B | 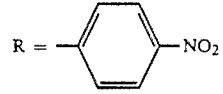 |

TABLE V-continued

7-Alkoxydithio-9a-methoxymitosanes

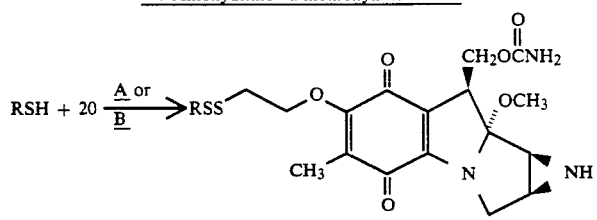

| Example No. | Thiol (RSH) | Procedure | Product |
|---|---|---|---|
| 30 | 2-nitro-4-mercaptobenzoic acid | B | R = 4-(NO2)-2-(COO⁻Na⁺)-phenyl |
| 31 | 4-mercaptopyridine | A | R = 4-pyridyl |
| 32 | 2-mercaptomethyl-1-methylimidazole | A | R = —CH₂—(1-methylimidazol-2-yl) |
| 33 | glutathione | B | R = —CH₂CH(NHCOCH₂CH₂CH(NH₂)COO⁻Na⁺)(CONHCH₂COO⁻Na⁺) |
| 34 | dimethylamine ethanethiol | B | R = —CH₂CH₂N(CH₃)₂ |

TABLE VI

7-Alkoxydithio-9a-methoxymitosanes

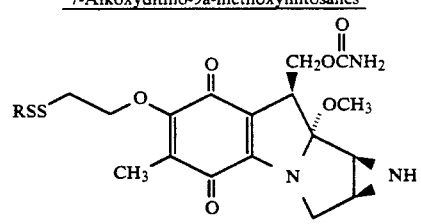

| Example No. | Formula | ¹H NMR Data (Pyridine-d₅)ᵃ (δ, ppm) | UV (CH₃OH) (λ$_{max}$, nm) | IR (KBr) (ν$_{max}$, cm⁻¹) |
|---|---|---|---|---|
| 21 | R = —CH₂CH₂OC(O)CH₃ | 1.76(s, 3H), 1.84(s, 3H), 1.97(t, 1H, 7.9Hz), 2.59(bs, 1H), 2.87(t, 2H, 6.7Hz), 2.96(t, 2H, 6.2Hz), 2.99(bs, 1H), 3.07(s, 3H), 3.37 (d, 1H, 12.1Hz), 3.84(dd, 1H, 11.2, 4.3Hz), 4.05(d, 1H, 12.1Hz), 4.27 (t, 2H, 6.7Hz), 4.56(m, 2H), 4.92(t, 1H, 10.8Hz), 5.25(dd, 1H, 11.2, 4.3Hz). | 520, 324, 216 | 3370, 3310, 2930, 1740, 1720, 1640, 1560, 1520, 1 335, 1220, 1200, 1065, 1030. |
| 22 | R = —CH₂CH(OH)CH₂OH | 1.77(s, 3H), 1.99(bs, 1H), 2.60(bs, 1H), 3.03(t, 2H, 6.3Hz), 3.00(m, 1H), 3.07(s, 3H), 3.15(m, 1H), 3.28(dd, 1H, 4.5, 13.2Hz), 3.37(d, 1H, 12.4Hz), 3.84(dd, 1H, 4.5, 11.2Hz), 3.94(bs, 2H), 4.06(d, 1H, 12.4Hz), 4.28(bs, 1H), 4.57(m, 1H), 4.64(m, 1H), 4.92(1H, t, 10.6Hz), 5.25(dd, 1H), 6.29(bs, 1H), 6.69(bs, 1H), 7.5( m, 2H). | 215, 324, 520 | 3440, 2965, 1720, 1655, 1635, 1580, 1455, 1410, 1340, 1305, 1215, 1070, 1020. |

TABLE VI-continued

7-Alkoxydithio-9a-methoxymitosanes

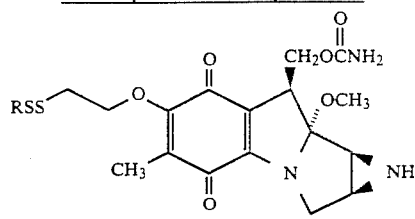

| Example No. | Formula | $^1$H NMR Data (Pyridine-$d_5$)$^a$ (δ, ppm) | UV (CH$_3$OH) ($\lambda_{max}$, nm) | IR (KBr) ($\nu_{max}$, cm$^{-1}$) |
|---|---|---|---|---|
| 23 | R = —CH$_2$CH$_2$COO$^-$Na$^+$ | 1.77(s, 3H), 2.60(bs, 1H), 2.78(t, 2H, 7.4Hz), 2.94(m, 3H), 3.00(s, 3H), 3.17(t, 2H, 7.4Hz), 3.38(d, 1H, 12.4Hz), 3.83(dd, 1H, 4.0, 11.0Hz), 4.06(d, 1H, 12.5Hz), 4.58(m, 2H), 4.84(m, 1H), 5.20(dd, 1H, 4.1, 10.6Hz), 7.64(m, 2H). | 215, 323, 510 | 3430, 2920, 1715, 1650, 1620, 1575, 1450, 1405, 1340, 1300, 1210, 1110, 1065. |
| 24 | R = CH$_2$CH(NH$_2$)COOH | 1.92(s, 3H), 2.95-3.15(m, 5H), 3.29 (s, 3H), 3.36(dd, 1H, 4.0, 15.0Hz), 4.02 (d, 1H, 13Hz), 4.10(dd, 1H, 4.0, 8.7Hz). 4.30(t, 1H, 10.5Hz), 4.48(m, 2H), 4.66 (dd, 1H, 4.8, 10.8Hz). | 216, 324, 381, 526 | 3430, 2920, 1715, 1635, 1575, 1495, 1450, 1340, 1300, 1210, 1060. |
| 25 | R = —C$_6$H$_5$ (phenyl) | 1.75(s, 3H), 1.99(bs, 1H), 2.61(bs, 1H), 2.98(m, 3H), 3.08(s, 3H), 3.39(d, 1H), 3.82(dd, 1H, 4.3, 11.0Hz), 4.06(d, 1H, 12.4Hz), 4.49(m, 1H), 4.57(m, 1H), 4.92 (m, 1H), 5.23(dd, 1H, 4.3, 11.0Hz), 7.11 (d, 1H, 7.2Hz), 7.19(dd, 2H, 7.2, 7.2Hz), 7.50(d, 2H, 7.2Hz). | 206, 324, 524 | 3440, 2920, 1715, 1650, 1630, 1575, 1450, 1335, 1300, 1210, 1105, 1055. |
| 26 | R = —C$_6$H$_4$—NO$_2$ (para) | 1.73(s, 3H), 1.94(m, 1H), 2.57(bs, 1H), 2.95(bs, 1H), 3.00(t, 2H), 3.04(s, 3H), 3.35(d, 1H, 12.1Hz), 3.79(dd, 1H, 4.2, 11.0Hz), 4.02(d, 1H, 12.1Hz), 4.53(m, 2H), 4.86(t, 1H, 11.0Hz), 5.20(dd, 1H, 4.2, 11.0Hz), 7.55(d, 2H, 8.8Hz), 8.02 (d, 2H, 8.8Hz). | 322, 215 | 3460, 3290, 2940, 1715, 1645, 1620, 1570, 1505, 1445, 1400, 1335, 1295, 1210, 1105, 1055. |
| 27 | R = —C$_6$H$_4$—OCH$_3$ (para) | 1.73(s, 3H), 2.00(m, 1H), 2.69(bs, 1H), 3.00(bs, 1H), 3.02(t, 2H), 3.08(s, 3H), 3.37(d, 1H, 12.0Hz), 3.51(s, 3H), 3.84(dd, 1H, 4.2, 11.0Hz), 4.06(d, 1H, 12.5Hz), 4.59(m, 2H), 4.93(t, 1H, 10.6Hz), 5.27(dd, 1H, 4.2, 11.0Hz), 6.84(d, 2H, 8.7Hz), 7.50(d, 2H, 8.7Hz). | 321, 236 | 3460, 3300, 2930, 1715, 1625, 1570, 1490, 1440, 1400, 1330, 1295, 1245, 1210, 1170, 1100, 1055, 1020. |
| 28 | R = —C$_6$H$_4$—NH$_2$ (para) | 1.74(s, 3H), 2.05(t, 1H, 6.6Hz), 2.60(bs, 1H), 2.96-3.11(m, 3H), 3.07(s, 3H), 3.37(d, 1H, 12.5Hz), 3.84(dd, 1H, 4.2, 11.0Hz), 4.09 (d, 1H, 12.5Hz), 4.53(m, 2H), 4.96 (t, 1H, 10.6Hz), 5.41(dd, 1H, 4.2, 11.0Hz), 5.84(bs, 1H), 6.72(d, 2H, 8.2Hz), 7.37(d, 2H, 8.2Hz). | 318, 252 | 3450, 3370, 2920, 1720, 1630, 1575, 1495, 1450, 1410, 1335, 1300, 1210, 1105, 1065. |
| 29 | R = —C$_6$H$_4$—COO$^-$Na$^+$ (ortho) | 1.76(s, 3H), 1.95(m, 1H), 2.59(bs, 1H), 2.90(t, 2H, 6.2Hz), 2.95(bs, 1H), 3.06(s, 3H), 3.38(d, 1H, 12.8Hz), 3.80(dd, 1H, 4.2, 11.0Hz), 4.05(d, 1H, 12.4Hz), 4.55(m, 2H), 4.87(m, 1H), 5.18(dd, 1H, 4.2, 10.4Hz), 7.08(t, 1H, 7.4Hz), 7.23(dd, 1H, 7.8, 7.4Hz), 7.5(bs, 2H), 8.25(d, 1H, 8.1Hz), 8.47(d, 1H, 7.7Hz). | 214, 246, 320, 524 | 3390, 3300, 2930, 1720, 1665, 1580, 1555, 1455, 1390, 1340, 1305, 1215, 1110, 1070, 1025. |
| 30 | R = —C$_6$H$_3$(NO$_2$)(COO$^-$Na$^+$) | 1.75(s, 3H), 2.58(bs, 1H), 2.93(t, 2H, 6.3Hz), 2.90(m, 1H), 3.38(d, 1H, 520 12.8Hz), 3.82(dd, 1H, 4.3, 10.9Hz), 4.06(d, 1H, 12.1Hz), 4.53(m, 2H), 4.88 (t, 1H, 10.5Hz), 5.21(dd, 1H, 4.2, 10.7Hz), 7.45(d, 1H, 8.5Hz), 7.65 (d, 1H, 8.3Hz), 8.14(bs, 1H). | 215, 321, 520 | 3440, 2930, 1720, 1620, 1580, 1520, 1450, 1400, 1340, 1215, 1070 |

TABLE VI-continued
7-Alkoxydithio-9a-methoxymitosanes

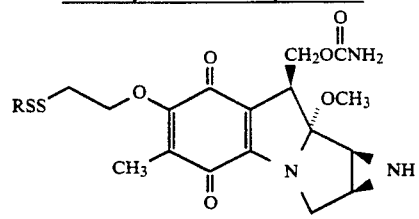

| Example No. | Formula | $^1$H NMR Data (Pyridine-$\underline{d}_5$)$^a$ (δ, ppm) | UV (CH$_3$OH) ($\lambda_{max}$, nm) | IR (KBr) ($\nu_{max}$, cm$^{-1}$) |
|---|---|---|---|---|
| 31 | R = (4-pyridyl) | 1.76(3H, s), 1.95(bs, 1H), 2.60(bs, 1H), 3.01(t, 2H, 6.1Hz), 3.00(m, 1H), 3.08(s, 3H), 3.39(d, 1H, 11.5Hz), 3.83(dd, 1H, 4.2, 11.0Hz), 4.07(d, 1H, 12.4Hz), 4.52(m, 2H), 4.90(bs, 1H), 5.25(dd, 1H, 4.3, 10.5Hz), 7.39(dd, 2H, 1.5, 4.5Hz), 7.6(m, 2H), 8.48(dd, 2H, 1.5, 4.5Hz). | 215, 241, 323, 522 | 3430, 2920, 1720, 1650, 1630, 1575, 1450, 1405, 1335, 1300, 1210, 1065. |
| 32 | R = —CH$_2$—(1-methylimidazol-2-yl) | 1.74(s, 3H), 2.59(bs, 1H), 2.73(t, 2H, 6.4Hz), 2.98(d, 1H, 4.2Hz), 3.08(s, 3H), 3.40(m, 1H), 3.43(s, 3H), 3.84(dd, 1H, 4.4, 11.0Hz), 4.06(d, 1H, 12.5Hz), 4.11(s, 2H), 4.46(m, 2H), 4.89(m, 1H), 5.25(dd, 1H, 4.4, 10.5Hz), 6.95(q, 2H). | 218, 323, 520 | 3430, 2960, 1720, 1650, 1630, 1580, 1490, 1450, 1335, 1300, 1210, 1105, 1065. |
| 33 | R = —CH$_2$CH(NHCOCH$_2$CH$_2$CHCOO$^-$Na$^+$)(CONHCH$_2$COO$^-$Na$^+$) with NH$_2$ | 1.91(s, 3H), 2.16(dd, 2H, 7.4, 14.2Hz), 2.55(dt, 2H, 2.3, 8.2Hz), 2.95–3.10 (m, 5H), 3.28(s, 3H), 3.28(dd, 1H, 4.6, 14.1Hz), 3.61(d, 1H, 13.1Hz), 3.70(dd, 1H, 4.4, 10.5Hz), 3.70–3.90 (m, 4H), 4.02(d, 2H, 13.1Hz), 4.30 (t, 1H, 10.5Hz), 4.46(m, 2H), 4.65(dd, 1H, 4.5, 10.7Hz). | 326, 366, 524 | 3380, 3290, 2920, 1715, 1650, 1635, 1580, 1455, 1405, 1340, 1300, 1210, 1105, 1065, 1030. |
| 34 | R = CH$_2$CH$_2$N(CH$_3$)$_2$ | 1.77(s, 3H), 1.93(bs, 1H), 2.14(s, 6H), 2.61(m, 3H), 2.80–3.05(m, 5H), 3.08(s, 3H), 3.40(m, 1H), 3.84(dd, 1H, 4.3, 10.3Hz), 4.06 (d, 1H, 12.5Hz), 4.57(m, 2H), 5.26(dd, 1H, 4.3, 10.3Hz) | — | — |

$^a$D$_2$O was used for mitosanes of Examples 24 and 33.

We claim:

1. A compound of the Formula IX

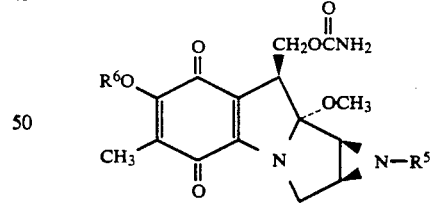

wherein $R^6$ is 2-(4-morpholinyl)ethyl and $R^5$ is hydrogen.

* * * * *